United States Patent [19]

Kiske et al.

[11] Patent Number: 6,009,871
[45] Date of Patent: Jan. 4, 2000

[54] VENTILATING APPARATUS

[75] Inventors: Siegfried Kiske, Krummesse; Karsten Hoffmann, Griebel, both of Germany

[73] Assignee: Drägerwek Aktiengesellschaft, Lubeck, Germany

[21] Appl. No.: 08/968,069

[22] Filed: Nov. 12, 1997

[30] Foreign Application Priority Data

Nov. 14, 1996 [DE] Germany ............................ 196 47 058

[51] Int. Cl.[7] .................................................. A61M 16/00
[52] U.S. Cl. ................................. 128/204.21; 128/204.23; 128/203.28; 128/205.18; 128/203.12
[58] Field of Search ......................... 128/204.21, 204.23, 128/203.28, 203.12, 205.13, 205.18, 200.24

[56] References Cited

U.S. PATENT DOCUMENTS

| | | | |
|---|---|---|---|
| 4,262,686 | 4/1981 | Heim et al. ................................. | 137/7 |
| 5,005,570 | 4/1991 | Perkins ................................. | 128/204.24 |
| 5,119,810 | 6/1992 | Kiske et al. ......................... | 128/204.26 |
| 5,678,540 | 10/1997 | Kock et al. ........................ | 128/205.14 |
| 5,810,002 | 9/1998 | Dittmann ............................ | 128/203.12 |
| 5,823,186 | 10/1998 | Rossen et al. ...................... | 128/204.21 |

FOREIGN PATENT DOCUMENTS 29 45 472   5/1981   Germany ....................... A61M 17/00

*Primary Examiner*—John G. Weiss
*Assistant Examiner*—V. Srivastava
*Attorney, Agent, or Firm*—Walter Ottesen

[57] ABSTRACT

A ventilating apparatus includes a closed breathing loop (3) which is supplied with the gases needed for ventilation via a metering unit (9). The ventilating apparatus is improved in such a manner that the respiratory gas can be metered during the inspiration phase without affecting the respiratory gas stroke volume supplied to the patient. The ventilating apparatus includes a flow-measuring device (14) for detecting a gas volume ($V_F$) which is metered into the closed breathing loop (3) during the inspiration phase. A subtraction element (16) forms a difference volume ($V_T - V_F$) between the pump volume ($V_T$) and the gas volume ($V_F$). A switch (21) permits utilizing the difference volume ($V_T - V_F$) as a new adjusting value for the pump volume of the respiratory gas pump unit (2).

2 Claims, 1 Drawing Sheet

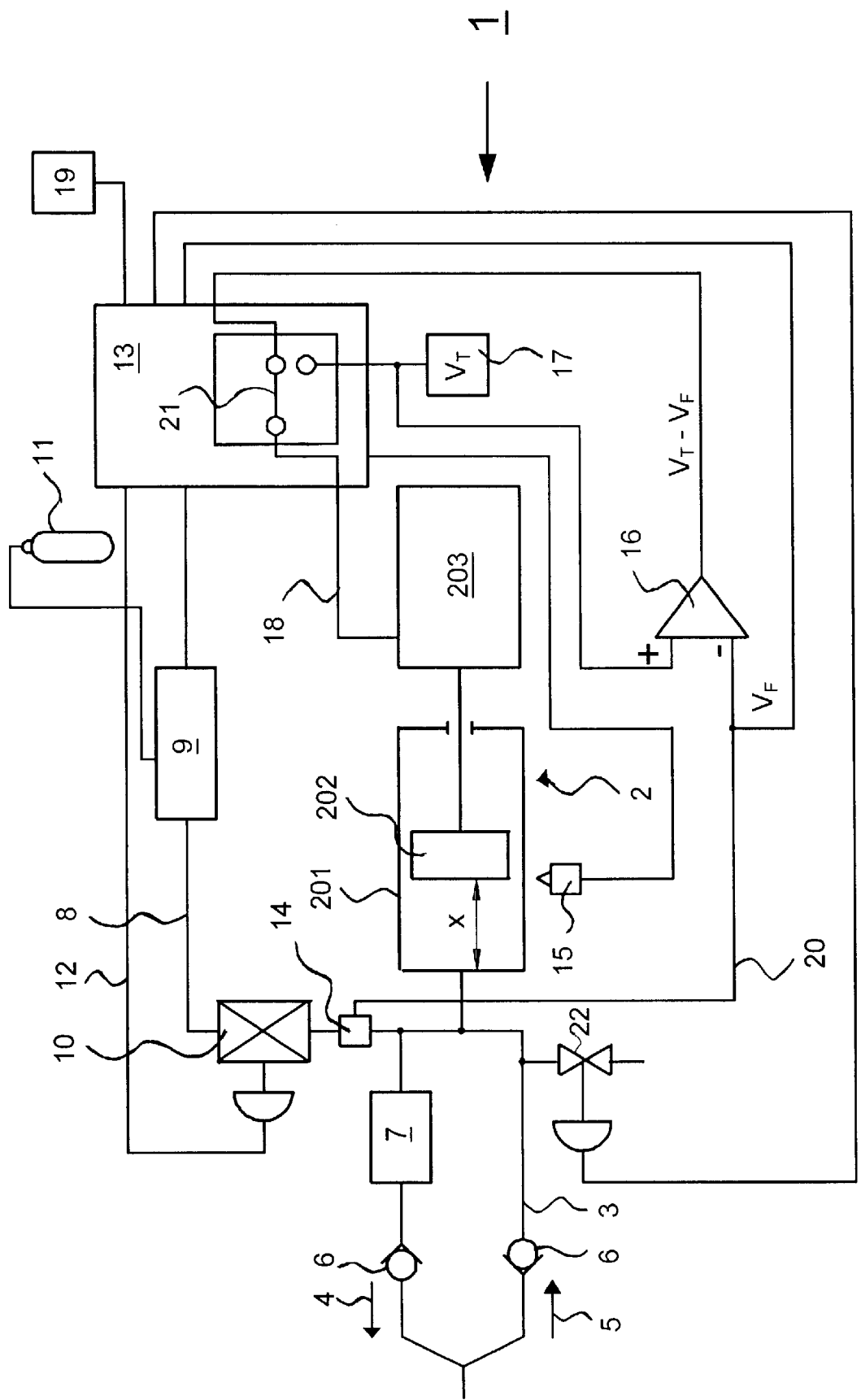

VENTILATING APPARATUS

FIELD OF THE INVENTION

The invention relates to a ventilating apparatus having a closed breathing loop which supplies the gases needed for ventilation via a metering unit.

BACKGROUND OF THE INVENTION

German patent publication 2,945,472 discloses a ventilating apparatus having a closed respiratory loop wherein respiratory gas is continuously metered into the breathing loop via a metering unit. The ventilating apparatus includes a ventilating bellows which compresses during the inspiration phase and decompresses during the expiration phase. The ventilation of a patient connected to the respiratory loop is made possible by means of this ventilating bellows. The stroke volume to be supplied to the patient can be adjusted by an adjusting device which limits the stroke of the bellows.

It is disadvantageous with this known ventilating apparatus that the stroke volume adjusted with the adjusting device is increased by the respiratory gas which flows in continuously from the metering device into the breathing loop. This influence becomes that much greater the lower the setting of the stroke volume is and the more respiratory gas is supplied by the metering unit to the breathing loop.

U.S. Pat. No. 5,119,810 is incorporated herein by reference and discloses a ventilating apparatus wherein the supply of fresh respiratory gas is interrupted during the inspiration phase by means of a valve in the connecting line between the metering unit and the breathing loop. It is disadvantageous that the metering unit must be designed either for a high gas flow, which occurs during the exhalation phase, or a buffer volume has to be provided rearward of the metering unit from which the required respiratory gas can be taken during the exhalation phase.

SUMMARY OF THE INVENTION

It is an object of the invention to provide a ventilating apparatus of the kind referred to above wherein it is possible to meter respiratory gas during the inspiration phase without affecting the respiratory gas stroke volume supplied to the patient.

The ventilating apparatus of the invention is for ventilating a patient during inspiration and expiration phases. The apparatus includes: a closed breathing loop; a metering unit for metering gases to the breathing loop needed for ventilating the patient thereby replenishing the quantity of respiratory gas consumed or lost to leakage; a respiratory gas pump unit connected to the closed breathing loop and the respiratory gas pump unit having a changeable volume so as to permit a predetermined pumped volume ($V_T$) of the respiratory gas to be pumped into the breathing loop during the inspiration phase; a metering unit for metering a gas volume ($V_F$) into the closed breathing loop during the inspiration phase; means for detecting the gas volume ($V_F$) metered into the closed breathing loop by the metering unit during the inspiration phase; means for forming a difference volume ($V_T$-$V_F$) between the predetermined pumped volume ($V_T$) and the gas volume ($V_F$); and, means for applying the difference volume ($V_T$-$V_F$) as a new adjusting value for the volume of respiratory gas pumped by the respiratory gas pump unit.

The advantage of the invention is seen in that, with a metering-in of respiratory gas into the breathing loop during inspiration, the metered-in volume is set off against the volume supplied by the respiratory gas pump unit. The patient then always receives the predetermined respiratory gas stroke volume independent of the quantity of the gas flow supplied during the inspiratory phase by the metering unit. In the ventilating apparatus of the invention, it is also possible to meter fresh respiratory gas into the breathing loop during the inspiration phase as well as during the expiration phase. In this way, the entire breathing cycle can be utilized for metering in respiratory gas flow without the respiratory gas stroke volume being changed during the inspiration phase by the respiratory gas supplied by the metering unit into the breathing loop. By utilizing the inspiration and expiration phases for metering in respiratory gas, a buffer volume is unnecessary which would provide the required respiratory gas during the expiration phase.

The gas volume supplied by the metering unit can be detected in different ways. The metering unit can comprise electrically drivable gas valves which operate between two defined positions "open" and "closed" and, during the position "open", a specific gas volume is permitted to flow through. Insofar as the metering unit is made of such electrically drivable gas valves, the gas volume can be determined from the drive of the valves. For this purpose, the valves are advantageously switched utilizing a pulse-modulation technique.

A metering unit of this kind is described in U.S. Pat. No. 4,262,686 which is incorporated herein by reference. On the other hand, the possibility is provided to detect the gas flow, which is supplied by the metering unit, with a flow-measuring device and the volume can be determined in a manner known per se by integrating the gas flow over time.

It is advantageous to bring the respiratory gas pump unit to standstill during the inspiration phase for metering small respiratory gas stroke volumes. The respiratory gas flow, which is required for a respiratory gas stroke, is generated in this case exclusively by the metering unit for fresh respiratory gas. This mode of operation is especially advantageous when ventilating newborns. In the ventilating apparatus disclosed in German Patent 2,945,472, another bellows size must be utilized for ventilating newborns or infants.

BRIEF DESCRIPTION OF THE DRAWING

The invention will now be described with reference to the single figure of the drawing which shows a schematic of the ventilating apparatus according to the invention.

DESCRIPTION OF THE PREFERRED EMBODIMENTS OF THE INVENTION

Reference numeral 1 identifies the ventilating apparatus of the invention. The ventilating apparatus includes a respiratory pump unit 2 which, for example, can comprise the combination of a cylinder 201 and a piston 202 as well as a drive 203 for actuating the piston. The respiratory gas pump unit 2 is connected to a breathing loop 3. The breathing loop 3 functions to convey the respiratory gas during inspiration to a patient (not shown) and to return the respiratory gas to the respiratory gas pump unit 2 during expiration of the patient. The flow direction of the respiratory gas during inspiration is shown by arrow 4 and during expiration by arrow 5.

The loop or movement of the respiratory gas is maintained by the respiratory gas pump unit 2 and the respiratory gas is guided via directional valves 6 in the loop as indicated by arrows 4 and 5. A carbon dioxide absorber 7 is provided in the breathing loop 3 for purifying the respiratory gas.

Respiratory gas can escape through possible leaks or is consumed during the ventilating cycle. This respiratory gas can be resupplied via a fresh gas line 8. Excess respiratory gas can escape from the breathing loop 3 at the end of the expiration phase via a discharge valve 22. For refilling the breathing loop with fresh respiratory gas, the fresh-gas line is connected via a cutoff valve 10 to a metering unit 9 for respiratory gas. The metering unit 9 receives the respiratory gas to be metered from a reservoir 11.

The cutoff valve 10 is connected to a control unit 13 via a line 12. The respiratory gas flow supplied by the metering unit 9 is detected by a flow-measuring device 14 downstream of the cutoff valve 10 and is converted into a volume signal $V_F$ by integrating over time. A fill-level indicator 15 indicates the position of the piston 202 within the cylinder 201. A signal line 20 from the flow-measuring device 14 is connected to an input of the subtraction element 16 which, in turn, is connected to the control unit 13. The respiratory stroke volume $V_T$, which is required for the ventilation, is inputted to the control unit 13 via a desired-value adjusting device 17. The output of the desired-value adjusting device 17 is connected to the second input of the subtraction element 16.

The desired respiratory gas stroke volume $V_T$ is adjusted via the desired-value adjusting device 17 and this corresponds to a corresponding maximum piston stroke (x) of the piston 202 within the cylinder 201. The maximum piston stroke is detected by the fill-level indicator 15.

The operation of the ventilating apparatus according to the invention will now be described.

The pump drive 203 receives signals for carrying out the inspiration strokes and expiration strokes from the control unit 13 via a line 18. Via a selection switch 19 connected to the control unit 13, the time point for metering fresh respiratory gas into the respiratory loop can be adjusted. This adjustment is either for inspiration or expiration as well as mixed for inspiration and expiration. A switch 21 is provided within the control unit 13 and connects the output of the subtraction element 16 via line 18 to the pump drive 203 for the case where respiratory gas is metered in during the inspiration phase. In contrast, for metering in respiratory gas during expiration, the line 18 is connected via the switch 21 to the desired-value adjusting device 17.

For the case of metering in respiratory gas during inspiration, the pump drive 203 receives a difference signal via the, line 18 as a control variable. The difference signal is the difference of the respiratory stroke volume desired value $V_T$ and the volume signal $V_F$ computed with the flow-measuring device. This difference signal $V_T$-$V_F$ is adjusted as a new desired value at the pump drive 203. When supplying fresh respiratory gas during inspiration, the pumped volume pumped into the breathing loop 3 is reduced by the volume $V_F$. For metering respiratory gas during expiration, the desired-value adjusting device 17 is, in contrast, connected directly to the line 18 leading to the pump drive 203.

The ventilating apparatus 1 of the invention furthermore affords the advantage that small respiratory stroke volumes can be metered with good accuracy in a simple manner. For this purpose, the selection switch 19 is switched to a position at which respiratory gas is metered during inspiration and the pump drive 203 is at standstill. The gas required for executing a respiratory stroke is then metered exclusively via the metering unit 9 and the cutoff valve 10 into the breathing loop 3 in that the cutoff valve 10 is switched for a short time into the open position during the inspiration phase. The metered-in respiratory gas volume $V_F$ is determined with the flow-measuring device 14 and transmitted to the control unit 13. Here, the respiratory gas volume $V_F$. is compared to a value adjusted at the desired-value adjusting device 17. For possible deviations, correspondingly more or less respiratory gas is metered by the metering unit 9 into the breathing loop 3 during the next respiratory stroke. This form of carrying out the respiratory strokes is especially advantageous in the area of newborn and infant ventilation.

It is understood that the foregoing description is that of the preferred embodiments of the invention and that various changes and modifications may be made thereto without departing from the spirit and scope of the invention as defined in the appended claims.

What is claimed is:

1. A ventilating apparatus for ventilating a patient during inspiration and expiration phases, the apparatus comprising:

a closed breathing loop;

a dosing unit for dosing gases to said breathing loop needed for ventilating the patient thereby replenishing the quantity of respiratory gas consumed or lost to leakage;

a respiratory gas pump unit connected to said closed breathing loop and said respiratory gas pump unit having a changeable volume so as to permit a predetermined pumped volume ($V_T$) of said respiratory gas to be pumped into said breathing loop during said inspiration phase;

a metering unit for metering a gas volume ($V_F$) into said closed breathing loop during said inspiration phase;

means for detecting said gas volume ($V_F$) metered into said closed breathing loop by said metering unit during said inspiration phase;

means for forming a difference volume ($V_T$-$V_F$) between said predetermined pumped volume ($V_T$) and said gas volume ($V_F$); and, means for applying said difference volume ($V_T$-$V_F$) as a new adjusting value for the volume of respiratory gas pumped by said respiratory gas pump unit.

2. The ventilating apparatus of claim 1, further comprising means for bringing said respiratory gas pump unit to standstill during said inspiration phase.

* * * * *